US008538504B2

(12) United States Patent
Kleen et al.

(10) Patent No.: US 8,538,504 B2
(45) Date of Patent: Sep. 17, 2013

(54) METHOD FOR MERGING MEDICAL IMAGES

(76) Inventors: Martin Kleen, Neunkirchen (DE); Marcus Pfister, Erlangen (DE); Norbert Rahn, Forchheim (DE)

(*) Notice: Subject to any disclaimer, the term of this patent is extended or adjusted under 35 U.S.C. 154(b) by 1648 days.

(21) Appl. No.: 11/007,492

(22) Filed: Dec. 8, 2004

(65) Prior Publication Data

US 2005/0203420 A1 Sep. 15, 2005

(30) Foreign Application Priority Data

Dec. 8, 2003 (DE) ................................. 103 57 184

(51) Int. Cl.
*A61B 5/05* (2006.01)

(52) U.S. Cl.
USPC ............ 600/407; 600/410; 600/437; 600/458

(58) Field of Classification Search
USPC ......... 600/476, 407, 410, 414, 415, 423–427, 600/431
See application file for complete search history.

(56) References Cited

U.S. PATENT DOCUMENTS

| | | | | |
|---|---|---|---|---|
| 5,217,456 A * | 6/1993 | Narciso, Jr. | | 606/15 |
| 5,827,190 A * | 10/1998 | Palcic et al. | | 600/476 |
| 5,875,782 A * | 3/1999 | Ferrari et al. | | 128/898 |
| 6,148,095 A * | 11/2000 | Prause et al. | | 382/131 |
| 6,171,303 B1 * | 1/2001 | Ben-Haim et al. | | 606/15 |
| 6,247,812 B1 * | 6/2001 | Miehle et al. | | 351/206 |
| 6,317,621 B1 * | 11/2001 | Graumann et al. | | 600/424 |
| 6,359,960 B1 * | 3/2002 | Wahl et al. | | 378/20 |
| 6,422,994 B1 * | 7/2002 | Kaneko et al. | | 600/160 |
| 6,470,207 B1 * | 10/2002 | Simon et al. | | 600/426 |
| 6,490,467 B1 * | 12/2002 | Bucholz et al. | | 600/407 |
| 6,537,211 B1 * | 3/2003 | Wang et al. | | 600/178 |
| 6,549,802 B2 * | 4/2003 | Thornton | | 600/426 |
| 7,181,265 B2 * | 2/2007 | Sendai | | 600/476 |
| 2001/0029334 A1 * | 10/2001 | Graumann et al. | | 600/437 |
| 2002/0018588 A1 * | 2/2002 | Kusch | | 382/131 |
| 2002/0042568 A1 * | 4/2002 | Fuderer et al. | | 600/410 |
| 2002/0049375 A1 * | 4/2002 | Strommer et al. | | 600/407 |
| 2002/0050988 A1 * | 5/2002 | Petrov et al. | | 345/418 |
| 2002/0077540 A1 * | 6/2002 | Kienzle, III | | 600/424 |

(Continued)

FOREIGN PATENT DOCUMENTS

| | | |
|---|---|---|
| DE | 44 45 214 A1 | 6/1996 |
| DE | 10015815 A1 | 10/2001 |
| EP | 1 210 907 A1 | 6/2002 |

OTHER PUBLICATIONS

Mahmood et al., "Bear-Infrared Optical Imaging of Protease Activity for Tumor Dection", Radiology, Dec. 1999, pp. 866-870, vol. 213, No. 3.

*Primary Examiner* — Tse Chen
*Assistant Examiner* — Mark Remaly

(57) ABSTRACT

A method for the merged display of first image information captured using a first imaging device with second image information captured using a second imaging device is provided. The first imaging device records fluorescence images of the area under examination. A second 3D image data record of the area under examination is recorded using an examination procedure based on electromagnetic radiation, such as computer tomography (CT) or magnetic resonance imaging (MRI). The 3D fluorescence image data record and the second 3D image data record are registered with one another, and one or more fluorescence-optically marked, relevant areas of the examination volume, on the basis of the mapping rules determined by the registration process, are displayed on a monitor.

10 Claims, 1 Drawing Sheet

(56) References Cited

U.S. PATENT DOCUMENTS

| | | | |
|---|---|---|---|
| 2002/0122576 A1* | 9/2002 | Weese et al. | 382/131 |
| 2002/0193677 A1 | 12/2002 | Thornton | |
| 2003/0129579 A1* | 7/2003 | Bornhop et al. | 435/4 |
| 2003/0130576 A1* | 7/2003 | Seeley et al. | 600/426 |
| 2003/0181809 A1* | 9/2003 | Hall et al. | 600/425 |
| 2003/0208116 A1 | 11/2003 | Liang et al. | |
| 2004/0015062 A1* | 1/2004 | Ntziachristos et al. | 600/312 |
| 2004/0024311 A1* | 2/2004 | Quaid, III | 600/428 |
| 2004/0034302 A1* | 2/2004 | Abovitz et al. | 600/428 |
| 2004/0049109 A1* | 3/2004 | Thornton | 600/427 |
| 2004/0102697 A1* | 5/2004 | Evron | 600/424 |
| 2004/0247076 A1* | 12/2004 | Navab et al. | 378/63 |
| 2005/0165303 A1* | 7/2005 | Kleen et al. | 600/424 |
| 2005/0171428 A1* | 8/2005 | Fichtinger et al. | 600/426 |
| 2005/0182321 A1* | 8/2005 | Frangioni | 600/431 |

\* cited by examiner

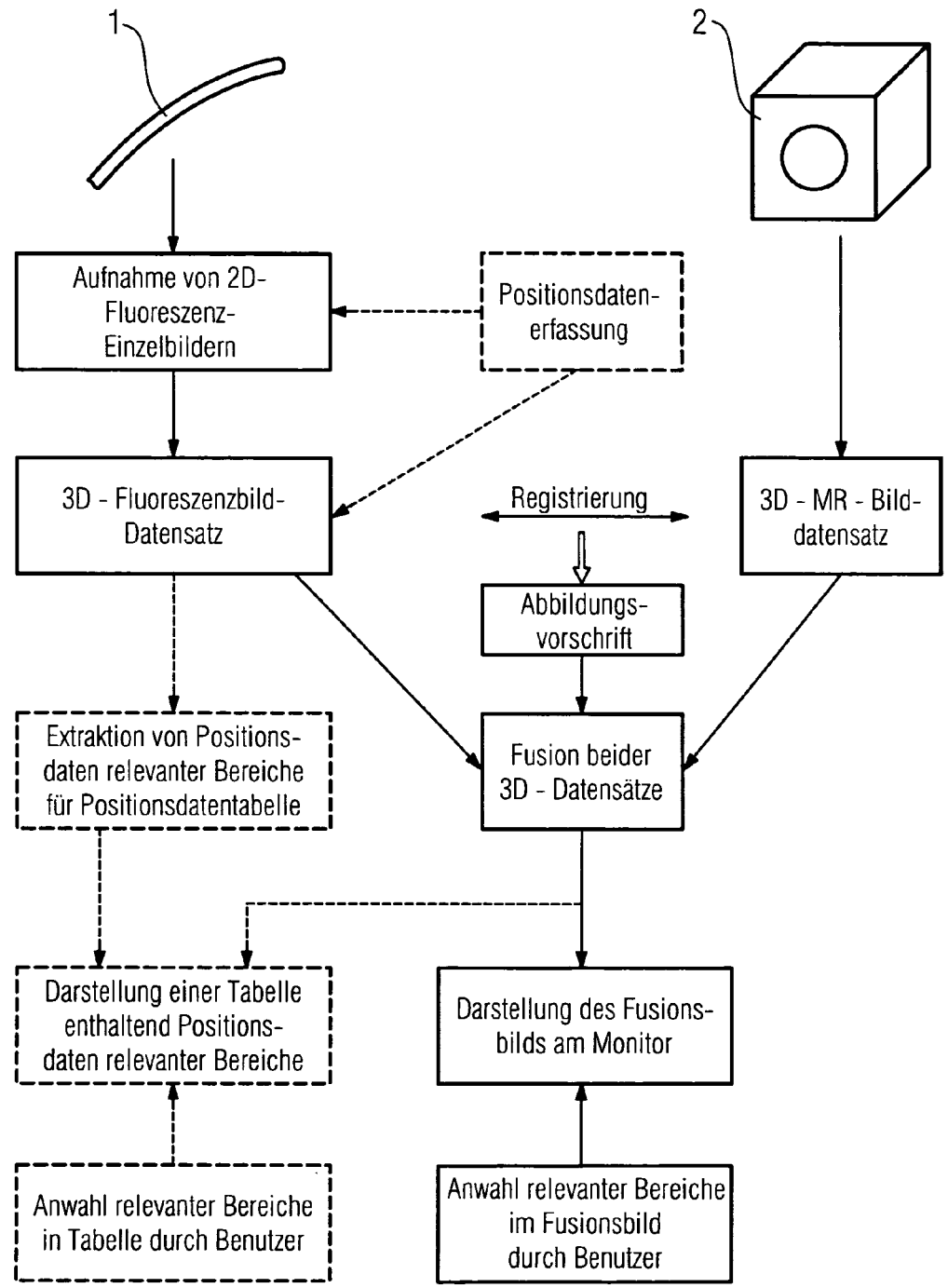

METHOD FOR MERGING MEDICAL IMAGES

CROSS REFERENCE TO RELATED APPLICATIONS

This application claims priority to the German application No. 10357184.1, filed Dec. 8, 2003 which is incorporated by reference herein in its entirety.

FIELD OF INVENTION

The invention relates to a method for the merged display of first image information captured using a first imaging device with second image information captured using a second imaging device, whereby said image information relates to the same area of examination in the human or animal body, in particular a hollow organ.

BACKGROUND OF INVENTION

Fluorescent metabolic substances are known from the field of biotechnology. These substances either accumulate solely in certain areas such as—for example—tumors, inflammations or other specific centers of morbidity, and are therefore only present locally, or they are distributed throughout the body but their fluorescent property is only activated in certain regions in particular, e.g. due to tumor-specific enzyme activities. Because of their fluorescent property these substances can be used as markers or marking substances in order to mark or even record a certain area, e.g. an already pathological area. A region that has been fluorescently marked in this way is identified by illumination of said region with light from a special excitation wavelength of the fluorescent dye and detection of the emitted light in the corresponding emission wavelength of the fluorophore. Potential applications of this examination procedure are all near-surface organs within light penetration range and which develop carcinomas, inflammatory processes or other diseases that are receptive to the application of fluorescent substances. Preferred applications would, for example, be examinations of the prostate gland, bowel, gullet, bronchial tubes or vascular system.

SUMMARY OF INVENTION

In order to make proper use of the diagnostic information content of such fluorescent Markings it would be necessary to be able to record the markings locally using a minimally invasive process. However, it would also be necessary to be able to show this image information to the doctor in a meaningful way to enable him or her to produce an accurate diagnosis from the image information recorded.

This invention is therefore intended to address the problem of specifying a method that offers the doctor a meaningful, diagnostically applicable display of image information.

This problem is resolved by a method and their preferred embodiments laid down in the claims.

According to the invention, the merging of two three-dimensional image data records, the first of these being the fluorescence image data record, and the second being a three-dimensional image data record taken using a different examination procedure, e.g. magnetic resonance imaging, computer topography, ultrasound scanning or x-rays, and showing the same area under examination. This enables the fluorescence-optically marked areas that were recorded in the fluorescence three-dimensional image via the fluorescence-optical examination, to be displayed, accurately positioned, in a three-dimensional image of the area under examination. Not only does this provide the doctor with information about the places in the area under examination that are fluorescence-optically marked and are possibly already pathological, but the merging also enables the doctor to see the anatomical structures of the area under examination, and also, therefore, the marked areas in their anatomical context. This combined image makes it possible for the doctor to achieve a significantly improved diagnosis and localization of the fluorescence-marked regions in the area under examination, enabling a far more accurate and meaningful diagnosis to be reached.

In the procedure, first of all a plurality of two-dimensional images of the area under examination, for example a hollow organ, are obtained using a continuous, controlled movement of a medical instrument such as a catheter, an endoscope, a laparoscope or a colonoscope, so that these individual images can be compiled into a three-dimensional fluorescence data record. This data record now also receives information about the fluorescence-optically marked areas, also referred to below as fluorescence focal points. This fluorescence data record is then registered with the 3D data record, for example taken by an MR system and containing high-resolution, three-dimensional anatomical image data of the same area under examination. This registration is used to determine a mapping rule that enables each pixel of the individual two-dimensional images on which both the fluorescence data record and the further 3D data record are based, and each voxel of the reconstructed volumes, to be mapped onto one another. The term registration is sufficiently well known in the field of digital image data processing and does not need to be defined in greater detail. After the mapping rule has been determined, therefore, it is possible for each voxel of the fluorescence three-dimensional image to be mapped onto the corresponding voxel in the 3D image of the MR picture. This also means, however, that it is possible for the fluorescence three-dimensional image, or the data record on which it is based, to be merged with the three-dimensional MR image or the data record on which it is based, and for a combined, merged image to be displayed on the monitor. Since the MR image (the same also applies for CT images or 3D angiograph or 3D ultrasound images) provides a detailed view of the anatomy of the area under examination, with high resolution and three-dimensionally, it is possible—advantageously—for the doctor, when viewing the merged image, to obtain highly accurate information regarding the anatomical conditions in the area under examination as well as anatomically relevant information with regard to the fluorescence-optically marked regions. Extremely accurate identification and localization of the relevant areas is therefore possible.

By using a medical instrument, which is to be introduced invasively into the area under examination, it is possible—to particularly advantageous effect—to use light excitation in the immediate locality, i.e. in the very area under examination. For example, a catheter would be used for examining a vessel (even inside the heart, for example), whereas a colonoscope would be used for bowel examinations. In each case the relevant instrument enables the excitation light to be emitted locally, and the light emitted in response to the fluorescence to be recorded locally. This response light may be light emitted by metabolic markers administered to the patient especially for this purpose, or light from the body's own substances that have had their fluorescent property activated owing to the existence of a center of morbidity or similar.

Since fluorescence-based imaging is based on the capturing of light emitted in response to excitation, said light being emitted only from such areas where fluorescent substances are concentrated, the recorded individual fluorescence images show bright areas where response light was emitted, whereas the other areas—where no light was emitted—are dark. To enable the fluorescence-optically relevant areas to be shown, an embodiment of the invention is available in which one or more fluorescently marked, relevant areas of the area under examination can be identified in the 3D fluorescence image data record in terms of their spatial position, and only these areas are displayed, accurately positioned, in the further three-dimensional image. Thus the bright, fluorescence-optically marked areas are extracted from the entire data record, and only this extracted, partial information is displayed in the merged image. This means that it is possible to merge only the extracted partial data with the further 3D data record, or to merge the two complete data records and carry out the described extraction while the actual merged image is being displayed. Identification of the relevant area or areas may usefully be carried out on the basis of the gray-scale values of the pixels in the individual images or the voxels of the three-dimensional image. As an alternative to the described extraction, it is possible for the complete fluorescence three-dimensional image to be superimposed over the further three-dimensional image, if necessary masking out voxels with predetermined gray-scale values. To avoid the image display being impaired in the merged image because of the presence, in the fluorescence three-dimensional image, of black areas in which—as described—no response light is emitted, the black three-dimensional area of the fluorescence three-dimensional image may—for example—be virtually masked out, since it can easily be captured on the basis of the local gray-scale values.

In order both to carry out the three-dimensional reconstruction and the registration with the further 3D data record, it is advisable for the positional data describing the spatial position of each individual fluorescence image to be recorded in a coordinates system of a positional registration system, simultaneously with the recording of the individual fluorescence images. An external positional registration system is used for this purpose, which interacts with a sensor on the medical instrument being introduced, e.g. a catheter. This sensor can be used advantageously to register movement in six degrees of freedom, these being the three spatial axes x, y and z, and the corresponding rotations around these axes. Such positional registration systems are known and primarily use electromagnetic coils and electromagnetic signals for recording movement and position. Since the further 3D record is also based on a separate coordinates system in which the position of each individual image is precisely defined, the registration and thus the recording of the mapping rule can be effected via the two separate coordinate systems.

As an alternative to this it is possible to reconstruct the fluorescence three-dimensional image on the basis of matching image areas in different individual images and to effect the registration with the further three-dimensional image on the basis of anatomical landmarks present in both three-dimensional images. No positional data is recorded in this case; the fluorescence three-dimensional reconstruction is effected rather by capturing matching image sections of consecutively recorded individual images which are then combined with one another, on the basis of these recorded matches, in order to reconstruct the image. Since the fluorescence three-dimensional image and the further three-dimensional image show the same area under examination, the same anatomical landmarks are also present in both images. The registration may then be effected on this basis, provided that these anatomical landmarks are also actually visible (for which the accumulation of fluorescent markers in these areas is required) in the fluorescence three-dimensional image. This will be the case primarily in cases of native fluorescence. A mapping rule can be determined in this way for each case, whereby said mapping rule permits the overlaying of the fluorescence focal points on the three-dimensional MR image, for example. At this point it should be mentioned that the data records on the basis of which the three dimensional images are generated (but not the three-dimensional images per se) are, of course, each registered with one another.

Various display methods may be used to display the merged three-dimensional image. The form of display ultimately depends on the form used to display the further three-dimensional image—e.g. the MR or CT image in which the relevant areas are shown overlaid. It is possible for the further three-dimensional image to be visualized as an "endoscopic view", in which the relevant areas are overlaid. Such a visualization, which is also known as a "fly-through", is suitable mainly for visualizing the interior of hollow organs and vessels. Regardless of the recording method used, the fluorescence focal points are overlaid as false-color-coded hotspots in the "endoscopic view" visualization of the further, anatomical 3D-data record, for example in order to visualize inflammatory processes in vessels.

It is also possible for the further three-dimensional image to be displayed as an MPR image (MPR=multi-planar reformatting), with the fluorescence focal points likewise being overlaid as false-color-coded hotspots in order to display the anatomy visualized in the MPR image and surrounding the fluorescence focal points.

It is also possible for the further three-dimensional image to be visualized as an MIP image (MIP=maximum intensity projection), with the fluorescence focal points likewise being overlaid as false-color-coded hotspots. An MIP image is ideal for the visualization of contrasted objects, e.g. vessels.

It is also possible for the three-dimensional image to be reproduced as an SSD image (SSD=surface shaded display), with the fluorescence focal points likewise being overlaid as false-color-coded hotspots.

Finally it is possible to use VRT imaging (VRT=volume rendered technique), in which the fluorescence focal points are likewise overlaid as false-color-coded hotspots. In this method the opacity of the VRT visualization can be modified with the help of a transfer function, such that the voxels displayed in the VRT visualization of the further volume have a lower opacity relative to the fluorescence focal points. This is achieved since the false-color-coded fluorescence areas are easily visible in the "translucent" anatomy.

The above list of display options is not conclusive and the invention is not limited to the options mentioned.

Since examination areas of virtually any size may be recorded using the examination procedures in question, it is desirable for the user to be able to display, quickly and easily, a particular area of interest in the examination volume. To facilitate this, a development of the invention makes provision whereby a relevant area of the examination volume can be selected by the user and the merged image showing this area is reproduced on the monitor. In this way it is possible, quickly and easily, to locate one or more fluorescence focal points in the merged data, since the user can "navigate" within the displayed image.

A first embodiment of this option makes provision whereby the user may select an area to be displayed using a table displayed on the monitor, said table containing the positional data of the individual relevant areas of the total examination volume. Thus, according to this embodiment of the invention, an area is selected and the view changed simply by selecting the area from the table, the positional data of said area having been recorded in the table. At the same time the positional data of the individual relevant areas can be determined automatically and recorded in the table on the basis of the individual fluorescence images or the fluorescence three-dimensional image. This means that the positional data is automatically extracted from the existing image data. This may take place, for example, as part of the area extraction process already described at the start, provided the corresponding positional data for the individual images is recorded. In the list, the individual extracted areas are allocated numbers (for example), so that the user can therefore purposefully "scroll" from area to area and can vary the displayed view accordingly.

In this context it is useful for the user to be able to set one or more entries for the positional data in the table. The user may therefore add supplementary information to the individual entries, for example to state that a particularly critical "vulnerable plaque" is present at a certain anatomical location, or to add any other comments that he or she may find helpful for the purpose of selection.

As an alternative to selection via the table, the image may also be varied whereby the user can select, using a movable marking device, a relevant area in the merged three-dimensional image displayed on the monitor, said area then being reproduced in the modified view. Using the marking device, for example the cursor, the user "clicks" on a displayed relevant area, for example, whereupon this area or the merged three-dimensional image is enlarged accordingly or otherwise displayed as modified, in order to show the selected area in even greater detail. The type of selection and/or display may vary depending on which visualization type is selected for the further three-dimensional image. In the case of an MIP image the three-dimensional image data record does not contain any depth information, since this display mode does not use sectional images but displays only voxels with a specific brightness from the entire data record. The MIP image is largely transparent and is also known as an "aquarium display". In order now to be able to show precisely the required area at the correct display level, in this case two MIP images are reproduced on the monitor, whereby said images show the area under examination from two directions that are preferably perpendicular to one another. Since the relevant area to be selected is visible in both images, the user must "click" on these two MIP images, whereupon the 3D position of the selected fluorescence focal point is selected in the three-dimensional data record and a correspondingly modified view may be displayed.

MPR, SSD and VRT images are, however, based on sectional images and the display also includes depth information. In this case it is possible to select the required focal point directly in the merged image and to "jump" to it.

BRIEF DESCRIPTION OF THE DRAWING

Other advantages, features and details of the invention are explained in the exemplary embodiment described below, with the help of the drawing.

This drawing shows a flow chart in schematic form, from which the basic process sequence may be seen.

DETAILED DESCRIPTION OF INVENTION

In the example shown, first of all a plurality of individual 2D fluorescence images are recorded using a medical instrument 1, e.g. a catheter, whereby said catheter is moved in a controlled manner through the hollow organ, for example. The catheter has an integrated means for administering an excitation light, which causes the fluorescent substance to emit a response light, and a means for recording the response light, for which purpose said catheter is coupled to suitable light sources/processing equipment which are not shown in greater detail here.

In parallel to the recording of individual images it is possible to record the positional data for each individual image, that shows in which position in a coordinates system of a positional data recording system (not shown in further detail) the individual image in question was recorded.

A 3D fluorescence image data record is then determined on the basis of the recorded individual 2D fluorescence images. This may be done using the positional data of the individual images if this has been recorded, or—alternatively—it is possible for the individual images to be linked to one another on the basis of matching image parts.

Using an external examination procedure 2, this being magnetic resonance imaging in the example shown, image information relating to the same area under examination was recorded earlier and a 3D MR image data record produced on the basis of this. This is fed to a processing device (not shown in greater detail here) which carries out the entire image data processing. In the next stage the 3D fluorescence image data record and the 3D MR image data record are registered with one another in order to determine a mapping rule that enables each voxel of the relevant three-dimensional image, which can be reconstructed from the 3D fluorescence image data record or 3D MR image data record, to be mapped onto the respective other three-dimensional image. Following registration it is also possible to allocate the voxels of each three-dimensional image, or the corresponding data, directly to one another according to the mapping rule.

In the next stage the two 3D data records are merged on the basis of the mapping rule that enables a merged image to be displayed on a monitor (not shown in greater detail). In this merged image, the relevant, fluorescence-optically marked areas are displayed as they appear from the fluorescence-optical catheter examination, combined with the accurate, high-resolution display of anatomical structures, obtained from the MR examination.

Various display methods could potentially be used for displaying three-dimensional MR images; these have already been described in detail above.

Since the main object of the method according to the invention is to display accurately the fluorescence-optically marked, possibly pathological areas in their actual anatomical environment, there are a number of potential options available for the overlaying of these areas on the three-dimensional MR image. Firstly, it is possible to extract from the merged 3D data images those areas that are contained in the 3D fluorescence image data record, and to display only these areas as being overlaid. Alternatively, it is possible to overlay the entire fluorescence three-dimensional image, while masking out—for example—the voxels which have a particular gray-scale value or which are above or below a defined gray-scale threshold, so that the areas in the fluorescent volume that are actually black and do not emit any response light are masked out.

It is also possible for the user to modify the displayed merged image and—particular—to jump to any relevant area as required. This makes it possible to locate and return to relevant areas in the displayed merged image. The user achieves this by selecting, using a suitable marking device (for example the screen cursor), a particular relevant area in the merged image, whereupon this area is enlarged, for example, or displayed centrally on the screen, or similar.

As an alternative to this option, this area selection could potentially be carried out using a table displayed on the monitor. For this purpose, a table containing positional data of the individual relevant areas is created, preferably by automatic means. Users can create this table themselves, for example, by "clicking" on the displayed areas using the screen cursor, whereupon the corresponding positional data is automatically determined and entered in a table. It is also possible, as shown in the diagram, to extract the positional data for the relevant areas directly after creating the 3D fluorescence image data record and to enter it into the table automatically. The extraction of data is relatively straightforward for the positional data recording described, since the relevant areas can be identified without further action using the gray-scale distribution in the three-dimensional image data record.

To make the corresponding selection the user now has only to select a specific area from the table, whereupon the corresponding variation in the three-dimensional image is automatically effected.

The invention claimed is:

1. A method for merging and displaying images captured by a first and a second imaging device, comprising:
   recording first image information including a plurality of two-dimensional images of an examination area comprising fluorescent and non-fluorescent areas, the recording of the first image information comprising fluorescence-based images using a medical instrument adapted to perform light-excitation of fluorescent areas of the examination area, the medical instrument introduced invasively into the examination area, by a first imaging device;
   generating a three dimensional fluorescence image data record related to the examination area using the plurality of two-dimensional images;
   recording a further three dimensional image data record of the examination area using a further medical examination procedure, by a second imaging device, wherein the medical examination procedure by the second imaging device is based on electromagnetic radiation;
   generating a further three dimensional image related to the examination area using the further three dimensional image data record;
   registering the three dimensional fluorescence image data record and the further three dimensional image data record with each another, wherein the registering of the three dimensional fluorescence image data record and the further three dimensional image data record with each another is based on anatomical landmarks present in both the three dimensional fluorescence image data record and the further three dimensional image data record;
   processing the fluorescence image data record of the examination area to identify at least one dark area corresponding to at least one non-fluorescent area of the examination area unresponsive to the light-excitation and at least one bright area corresponding to at least one fluorescent area of the examination area responsive to the light-excitation, said processing based on respective voxel values indicative of said at least one dark area and said at least one bright area;
   superimposing the three dimensional fluorescence image data record over the further three-dimensional image, wherein voxels indicative of said at least one dark area are omitted to mask out said at least one dark area; and
   displaying a fluorescence-optically marked relevant area of the examination area on a screen, wherein the fluorescence-optically marked relevant area consists only of said at least one bright area responsive to the light-excitation and is positioned in the further three-dimensional image so that its position in the further three-dimensional image is anatomically correct relative to the further three-dimensional image using mapping rules included in the registering of the three dimensional fluorescence image data record with the further three dimensional image data record.

2. The method according to claim 1, wherein positional data related to a spatial position of each two-dimensional image are recorded in parallel to recording the two-dimensional images using a coordinate system relative to a position detecting system.

3. The method according to claim 1, wherein the three dimensional fluorescence image data record is generated using corresponding image areas included in different two-dimensional images.

4. The method according to claim 1, wherein the further three-dimensional image is displayed as an element chosen from the group consisting of an "endoscopic view", an MPR image, an MIP image, an SSD image and a VRT image, wherein the relevant area is displayed using an overlay mechanism.

5. The method according to claim 1, wherein the relevant area is selected by a user and a merged image including the relevant area positioned in the further three-dimensional image is displayed on the screen.

6. The method according to claim 5, wherein the user selects the relevant area using a table displayed on the monitor, the table including positional data of a plurality of relevant areas.

7. The method according to claim 6, wherein the positional data are calculated automatically and recorded in the table using the two-dimensional images or the three dimensional fluorescence image data record.

8. The method according to claim 7, wherein the user enters one or more entries into the table.

9. The method according to claim 5, wherein the user selects the relevant area using a movable marking device, the relevant area subsequently displayed in a modified view.

10. A method for merging and displaying images captured by a first and a second imaging device, comprising:
   recording first image information including a plurality of two-dimensional images of an examination area comprising fluorescent and non-fluorescent areas, the recording of the first image information comprising fluorescence-based images using a medical instrument adapted to perform light-excitation of fluorescent areas of the examination area, the medical instrument introduced invasively into the examination area, by a first imaging device;
   generating a three dimensional fluorescence image data record related to the examination area using the plurality of two-dimensional images;
   recording a further three dimensional image data record of the examination area using a further medical examination procedure, by a second imaging device, wherein the medical examination procedure by the second imaging device is based on electromagnetic radiation;
   generating a further three dimensional image related to the examination area using the further three dimensional image data record;
   processing the fluorescence image data record of the examination area to identify at least one dark area corresponding to at least one non-fluorescent area of the examination area unresponsive to the light-excitation and at least one bright area corresponding to at least one fluorescent area of the examination area responsive to the light-excitation, said processing based on respective voxel values indicative of said at least one dark area and said at least one bright area;

extracting from the fluorescence image data record a partial image data comprising only said at least one bright area, wherein voxels indicative of said at least one dark area are omitted to mask out said at least one dark area;

registering the partial fluorescence image data record and the further three dimensional image data record with each another; and displaying a fluorescence-optically marked relevant area of the examination area on a screen, wherein the fluorescence-optically marked relevant area is positioned in the further three-dimensional image so that its position in the further three-dimensional image is anatomically correct relative to the further three-dimensional image using mapping rules included in the registering of the partial fluorescence image data record with the further three dimensional image data record.

* * * * *